United States Patent
Pauly et al.

(10) Patent No.: US 10,825,172 B2
(45) Date of Patent: Nov. 3, 2020

(54) MEDICAL IMAGE SEGMENTATION

(71) Applicant: Siemens Healthcare GmbH, Erlangen (DE)

(72) Inventors: Olivier Pauly, Munich (DE);
Florin-Cristian Ghesu, Erlangen (DE);
Cosmin Ionut Bercea, Nuremberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 56 days.

(21) Appl. No.: 16/393,011

(22) Filed: Apr. 24, 2019

(65) Prior Publication Data

US 2019/0347792 A1 Nov. 14, 2019

(30) Foreign Application Priority Data

May 9, 2018 (EP) .................................... 18171615

(51) Int. Cl.
*G06T 7/00* (2017.01)
*G06T 7/136* (2017.01)
(Continued)

(52) U.S. Cl.
CPC .......... *G06T 7/0012* (2013.01); *A61B 5/7267* (2013.01); *G06N 3/084* (2013.01); *G06T 7/11* (2017.01); *G06T 7/136* (2017.01); *G06K 9/6267* (2013.01); *G06K 9/66* (2013.01); *G06N 3/04* (2013.01); *G06T 2207/10088* (2013.01); *G06T 2207/20076* (2013.01);
(Continued)

(58) Field of Classification Search
CPC ...... A61B 5/7267; G06K 9/6267; G06K 9/66; G06N 3/04; G06N 3/084; G06T 2207/10088; G06T 2207/20076; G06T 2207/20081; G06T 2207/20084; G06T 2207/30004; G06T 7/0012; G06T 7/11
See application file for complete search history.

(56) References Cited

U.S. PATENT DOCUMENTS 9,811,906 B1 * 11/2017 Vizitiu ...................... G06T 7/11
2012/0070052 A1 * 3/2012 Maroy ...................... G06T 7/11
382/131
(Continued)

OTHER PUBLICATIONS

Milletari, Fausto et.al.: "Hough-CNN: Deep Learning for Segmentation of Deep Brain Regions in MRI and Ultrasound"; in: Preprint submitted to Pattern Recognition; pp. 1-34: 2016; XP-Nr. 055334930; DOI: 10.1016/j.cviu.2017.04.002.
(Continued)

*Primary Examiner* — David Bilodeau
(74) *Attorney, Agent, or Firm* — Harness, Dickey & Pierce, P.L.C.

(57) ABSTRACT

Systems and methods are disclosed for medical image processing using neural networks. A first and a second controller network share a memory to which both the first and second controller network can write data and from which both the first and the second controller network can read data. Reading and writing is performed by respective read and write heads which are advantageously neural networks trained how to write and read in an optimal way. The memory thus provides each controller network with context data generated by the respective other controller network.

21 Claims, 6 Drawing Sheets

(51) Int. Cl.
  *G06T 7/11* (2017.01)
  *A61B 5/00* (2006.01)
  *G06N 3/08* (2006.01)
  *G06K 9/62* (2006.01)
  *G06K 9/66* (2006.01)
  *G06N 3/04* (2006.01)

(52) U.S. Cl.
  CPC ............... *G06T 2207/20081* (2013.01); *G06T 2207/20084* (2013.01); *G06T 2207/30004* (2013.01)

(56) References Cited

U.S. PATENT DOCUMENTS

| | | | | |
|---|---|---|---|---|
| 2013/0094704 | A1* | 4/2013 | Hamadeh | G06T 7/11 382/103 |
| 2016/0335789 | A1* | 11/2016 | Zhang | G06T 7/194 |
| 2017/0091951 | A1* | 3/2017 | Yoo | G06T 7/11 |
| 2017/0323444 | A1* | 11/2017 | Fenchel | G06T 7/0014 |
| 2018/0174049 | A1* | 6/2018 | Pauly | G06T 7/0012 |
| 2019/0139216 | A1* | 5/2019 | Georgescu | G06T 7/11 |

OTHER PUBLICATIONS

Xie Yuanpu et al: "Spatial Clockwork Recurrent Neural Network for Muscle Perimysium Segmentation", Oct. 2, 2016 (Oct. 2, 2016), Medical Image Computing and Computer-Assisted; Intervention—MICCAI 2015: 18th International Conference, Munich, Germany, Oct. 5-9, 2015; Proceedings; [Lecture Notes in Computer Science; Lect.Notes Computer], Springer International Publishing, CH, XP047392498, ISSN: 0302-9743; ISBN: 978-3-030-00888.8; 2016.

Weston, Jason et al.:"Memory Networks"; in: Proceedings of ICLR; 2015; arXiv:1410.3916v11.

Chen, Liang-Chieh et al.:"Semantic Image Segmentation with Deep Convolutional Nets and Fully Connected CRFs"; in: Proceedings ICLR; 2015; arXiv:1412.7062v2.

Sukhbaatar, Sainbayar et al.:"End-To-End Memory Networks"; in: Advances in Neural Information Processing Systems 28; pp. 2440-2448; 2015.

Iglesias, Juan E. et al.:"Multi-Atlas Segmentation of Biomedical Images: A Survey"; in: Medical Image Analysis; vol. 24; No. 1; pp. 205-219; 2015; doi: 10.1016/j.media.2015.06.012.

Graves, Alex et al.:"Neural Turing Machines"; 2014; arXiv:1410.5401v2; Oct. 20, 2014; XP055239371; Retrieved from the Internet: URL:http://arvix.org/pdf/1410.5401v1.pdf.

Ronneberger, Olaf et al. "U-Net: Convolutional Networks for Biomedical Image Segmentation" Medical Image Computing and Computer-Assisted Intervention (MICCAI), Springer, LNCS, vol. 9351, pp. 234-241, 2015 // arXiv:1505.04597 [cs.CV].

Li, Xiaoxiao et al.:"Not All Pixels are Equal: Difficulty-aware Semantic Segmentation via Deep Layer Cascade"; 2017; arXiv:1704.01344.

Graves, Alex et al.:"Hybrid computing using a neural network with dynamic external memory"; in: Nature; vol. 538; pp. 471-476; 2016; doi:10.1038/nature20101.

Extended European Search Report 181716150 dated Oct. 18, 2017.

* cited by examiner

MEDICAL IMAGE SEGMENTATION

PRIORITY STATEMENT

The present application hereby claims priority under 35 U.S.C. § 119 to European patent application number EP 18171615.0 filed May 9, 2018, the entire contents of which are hereby incorporated herein by reference.

FIELD

Embodiments of the present invention generally relate to a system for medical image segmentation, or, in other words, a system for segmenting medical images; to a method for medical image segmentation, i.e. a method for segmenting medical images; to a computer-readable data storage medium; and/or to a computer program product.

BACKGROUND

Segmentation is a fundamental step in medical imaging towards computer aided diagnosis and intervention, treatment and clinical research. Segmentation may comprise determining which parts in a medical image of a patient belong to which organ of the patient.

A standard approach for medical image segmentation is multi-atlas label propagation (MALP). In MALP, a collection of atlases, i.e. labeled images e.g. manually by an expert, are used to estimate the segmentation of unseen data. A labelled image is, for example, an image together with a corresponding segmentation mask as the label provided by the expert.

State-of-the-art solutions usually perform computationally expensive non-linear registration of each atlas to unseen data and use the atlas labels directly as label proposals, see for example the following publications:

Milletari, F., Ahmadi, 5., Kroll, C., Plate, A., Rozanski, V. E., Maiostre, J., Levin, J., Dietrich, O., ErtlWagner, B., Botzel, K., Navab, N.: Hough-CNN: deep learning for segmentation of deep brain regions in MRI and ultrasound. CoRR abs/1601.07014 (2016). Cited in the following as "Milletari et al.", the entire contents of which are hereby incorporated herein by reference.

Iglesias J E, Sabuncu M R.: Multi-Atlas Segmentation of Biomedical Images: A Survey. Medical image analysis. 2015; 24(1):205-219. doi:10.1016/J.media.2015.06.012. Cited in the following as "Iglesias et al.", the entire contents of which are hereby incorporated herein by reference.

O. Ronneberger, P. Fischer and T. Brox.: U-Net: Convolutional Networks for Biomedical Image Segmentation. MICCAI, Springer, LNCS, Vol. 9351: 234-241, 2015.

Also known are image-to-image methods for image segmentation. Image-to-image methods leverage global context information by using the entire image to directly predict the complete segmentation mask in a single step. However, this results in a more complex learning task, with the models having to capture the complete variability in the shape and structure of the object, while being invariant to shifts.

Some image-to-image methods are described e.g. in the following publications:

L.-C. Chen, G. Papandreou, I. Kokkinos, K. Murphy and A. L. Yuille. Semantic image segmentation with deep convolutional nets and fully connected crfs. In ICLR, 2015

X. Li, Y. Liu, P. Luo, C. Loy and X. Tang.: Not all pixels are equal: Difficulty-aware semantic segmentation via deep layer cascade. arXiv:1704.01344, 2017.

Subsequently, label proposals are often aggregated or fused using a predefined strategy such as majority voting. These solutions are typically time-consuming, difficult to train or do not exploit long range anatomical context and constraints.

The following references describe some of the more recent advances in memory nets:

Graves, Alex, Wayne, Greg, and Danihelka, Ivo.: Neural turing machines. arXiv preprint, arXiv:1410.5401, 2014. Cited in the following as "Graves 2014", the entire contents of which is hereby incorporated herein by reference.

Graves, A., Wayne, 6., Reynolds, M., Harley, T., Danihelka, I., Grabska-Barwinska, A., . . . & Badia.: Hybrid computing using a neural network with dynamic external memory. Nature, 2016. Cited in the following as "Graves 2016", the entire contents of which is hereby incorporated herein by reference.

Sukhbaatar, Sainbayar, Szlam, Arthur, Weston, Jason, and Fergus, Rob.: End-to-end memory networks. Proceedings of NIPS, 2015.

Jason Weston, Sumit Chopra, and Antoine Bordes. Memory networks. In Proc. ICLR, 2015.

SUMMARY

Embodiments of the present invention provide a system and a method for medical image segmentation that is able to utilize long-range anatomical context information while at the same time ensuring high speed and reliability of the segmentation masks produced.

Specifically, according to a first embodiment, the invention provides a system for medical image segmentation, comprising:

an input module configured to provide a plurality of patches of an N-dimensional medical image to be segmented; a computing device configured to implement a trained first neural network as a first controller network and a trained second neural network as a second controller network; wherein the first controller network is configured to sequentially receive input data representing each of the plurality of patches in a first patch sequence, and to sequentially generate and output data indicative of a respective first patch segmentation mask candidate for each of the plurality of patches; wherein the second controller network is configured to sequentially receive input data representing each of the same plurality of patches in a second patch sequence, and to sequentially generate and output data indicative of a respective second patch segmentation mask candidate for each of the plurality of patches; wherein the second patch sequence is different from the first patch sequence; a memory shared by the first and the second controller network; wherein the first controller network is further configured to write data relating to a state of the first controller network to the memory, e.g. as context data;

wherein the second controller network is configured to read at least part of the data written by the first controller network from the memory and to utilize the read data when generating the data indicative of at least one of the second patch segmentation mask candidates; and wherein the computing device is further configured to generate, based on the data indicative of the first and second patch segmentation mask candidates, a final image segmentation mask for segmenting the N-dimensional medical image.

Additionally, according to a second embodiment, the invention provides a method for medical image segmentation, comprising:

providing a plurality of patches of an N-dimensional medical image to be segmented;

sequentially receiving, by a first trained neural network acting as a first controller network, input data representing each of the plurality of patches in a first patch sequence, sequentially generating and outputting, by the first controller network, data indicative of a respective first patch segmentation mask candidate for each of the plurality of patches;

sequentially receiving, by a second trained neural network acting as a second controller network, input data representing each of the plurality of patches in a second patch sequence, sequentially generating and outputting, by the second controller network, data indicative of a respective second patch segmentation mask candidate for each of the plurality of patches;

wherein the second patch sequence is different from the first patch sequence;

writing, by the first controller network, data relating to a state of the first controller network to a memory for at least the second controller network;

reading, by the second controller network, at least part of the data written by the first controller network from the memory;

utilizing, by the second controller network, the read data when generating the data indicative of at least one of the second patch segmentation mask candidates; and generating, based on the data indicative of the first and second patch segmentation mask candidates, a final image segmentation mask for segmenting the N-dimensional medical image.

Moreover, according to a third embodiment, the invention provides a computer-readable data storage medium comprising executable program code configured to, when executed, perform a method according to the second embodiment of the present invention.

According to a fourth embodiment, the invention provides a computer program product comprising executable program code configured to, when executed, perform a method according to the second embodiment of the present invention.

BRIEF DESCRIPTION OF THE DRAWINGS

The invention will be explained in greater detail with reference to example embodiments depicted in the drawings as appended.

The accompanying drawings are included to provide a further understanding of the present invention and are incorporated in and constitute a part of this specification. The drawings illustrate the embodiments of the present invention and together with the description serve to explain the principles of the invention. Other embodiments of the present invention and many of the intended advantages of the present invention will be readily appreciated as they become better understood by reference to the following detailed description. Like reference numerals designate corresponding similar parts.

DETAILED DESCRIPTION OF THE EXAMPLE EMBODIMENTS

Figure 1:
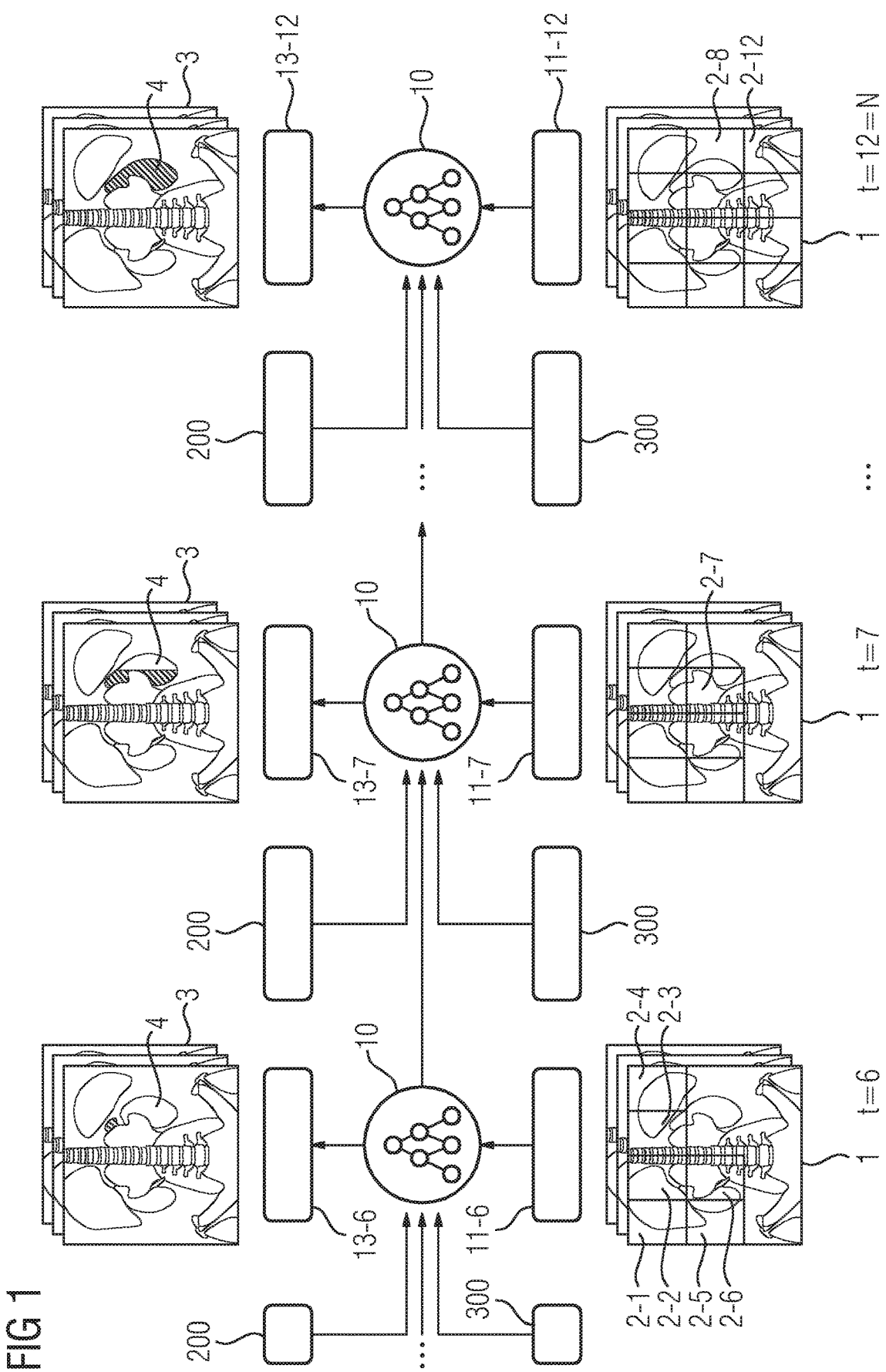
FIG. 1 schematically illustrates a procedure of patch-wise processing of an N-dimensional medical image.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

Specifically, according to a first embodiment, the invention provides a system for medical image segmentation, comprising:

an input module configured to provide a plurality of patches of an N-dimensional medical image to be segmented; a computing device configured to implement a trained first neural network as a first controller network and a trained second neural network as a second controller network; wherein the first controller network is configured to sequentially receive input data representing each of the plurality of patches in a first patch sequence, and to sequentially generate and output data indicative of a respective first patch segmentation mask candidate for each of the plurality of patches; wherein the second controller network is configured to sequentially receive input data representing each of the same plurality of patches in a second patch sequence, and to sequentially generate and output data indicative of a respective second patch segmentation mask candidate for each of the plurality of patches; wherein the second patch sequence is different from the first patch sequence; a memory shared by the first and the second controller network; wherein the first controller network is further configured to write data relating to a state of the first controller network to the memory, e.g. as context data;

wherein the second controller network is configured to read at least part of the data written by the first controller network from the memory and to utilize the read data when generating the data indicative of at least one of the second patch segmentation mask candidates; and wherein the computing device is further configured to generate, based on the data indicative of the first and second patch segmentation mask candidates, a final image segmentation mask for segmenting the N-dimensional medical image.

It should be understood that all neural networks mentioned herein are artificial neural networks and not biological neural networks.

The N-dimensional medical image may be simply a 2-dimensional medical image (N=2) such as a conventional X-ray or a 2D slice from magnetic resonance imaging (MRI). The N-dimensional image may also be a 3-dimensional medical image (N=3). Such a 3-dimensional medical image may be a medical image with three spatial directions such as an assembly of 2-dimensional slices e.g. from an MRI.

The 3-dimensional medical image may also be a 2-dimensional medical image combined with the time dimension, i.e. a two-dimensional video such as from a prolonged ultrasound examination.

The N-dimensional medical image may also be a 4-dimensional medical image (N=4) such as a medical image in three spatial dimensions combined with the time dimension, i.e. a three-dimensional video.

In all these examples, image segmentation may be advantageous.

The input module may be configured to provide the patches such that the entirety of patches, suitably arranged, comprise, or equal, the N-dimensional medical image. In some embodiments, the input module may be configured to provide patches that they, even taken together, only comprise, or equal, a part of the N-dimensional medical image. For example, in a clinic specialized for a certain organ, or when only a certain organ is to be examined, only patches may be provided that have a likelihood above a certain threshold value to contain a part of that certain organ. The likelihood may be determined by machine learning.

The input module, as well as further modules described in the foregoing, may be realized in hardware, such as a circuit or a printed circuit board and/or comprising transistors, logic gates and other circuitry. Additionally, the input module may be at least partially realized in terms of software. Accordingly, the input module may comprise, or be operatively coupled to, a processor and a memory storing a software or a firmware that is executed by the processor to perform the functions of the input module. Signals may be received by an input interface of the input module and signals that the processor of the input module creates may be outputted by an output interface of the input module. The input module may be implemented, at least partially, as a microcontroller, an ASIC, an FPGA and so on.

The input module may be configured to provide the patches such that the patches overlap at least some of their neighbours, or all of their neighbours, at least partially. The more the patches overlap, the easier it may become to fuse the individual patches and/or the patch segmentation masks and/or patch segmentation mask candidates together in order to form the N-dimensional medical image or the image segmentation mask, respectively. However, a larger overlap also means more processing power and memory used to determine redundant information. Overlap between neighbouring patches is not restricted to respective next-neighbours but may also include overlap with next-next-neighbours or even further neighbours.

The input module may be configured as a neural network, an optimal amount of overlap for neighbouring patches may be learned by machine learning, and the patches may then be provided with the determined optimal amount of overlap between neighbouring patches.

A computing device, as the term is used herein, should be understood to be any device for computing, i.e. for running a software or an algorithm. For example, the computing device may be a single processor core or a microprocessor. Preferably, the computing device is an array of processor cores or central processing units (CPUs). More preferably, the computing device is an array of graphical processing units (CPUs).

The computing device may be realized partially or completely by interconnected remote devices such as cloud computing servers and/or as a virtual machine.

A neural network, as the term is used herein, designates an artificial neural network. The term "trained neural network"

is used to emphasize that the neural networks have already been trained (e.g. using training data) in one of the ways known in the art.

A patch segmentation mask candidate, as the term is used herein, is a segmentation mask for a specific patch that is considered or proposed as a candidate for a final segmentation for that patch. A image segmentation mask for a segmentation of the N-dimensional medical image may be formed by aggregating the individual patch segmentation masks or patch segmentation mask candidates in a way according to the relationship of the patches with each other, e.g. depending on overlap and the like.

An image (or, respectively, patch) segmentation mask may separate any image (or, respectively, patch) into two regions, wherein one region corresponds to parts of the image (or, respectively, patch) within the mask, and a second region corresponds to parts of the image (or, respectively, patch) outside of the mask. For example, an image (or, respectively, patch) segmentation mask for identifying a human heart may, if correctly defined, indicate all parts of the image (or, respectively, patch) that belong to the human heart as within the mask and all parts of the image (or, respectively, patch) that do not belong to the human heart as outside of the mask.

The image segmentation mask may comprise more than two different regions, e.g. one region for each organ, or possible object of interested, within the N-dimensional medical image.

The patch sequence in which the input data is received by each controller network is preferably the same sequence in which the respective controller network processes the input data to generate the output data indicative of the patch segmentation mask candidates.

A memory, as the term is used herein, may be understood as any physical device or object, or plurality of physical devices or objects, that is capable of storing data. Moreover, the term may be understood as relating to a data structure within such a physical device or object or plurality. Sharing the memory means at the most basic level that the second controller network may read data that the first controller network has written to the memory. Preferably, the memory is realized as a semiconductor memory, for example as computer memory, volatile memory or non-volatile memory.

Sharing the memory may also comprise that both the first controller network and the second controller network (or, in case of more than two controller networks, all of the controller networks) are able to write to the same section or sections (or the entirety) of the memory, i.e. are able to overwrite what the other controller network has written. The section or sections may be physically separated from a remainder of the memory, or may be separated by a virtual division of the available memory space.

The system may be organized such that each controller network has access to a shared section of the shared memory as well as exclusive access to a private section of the memory to which no other controller network has access. Alternatively, the memory may be shared in its entirety, i.e. every data storage unit (e.g. bit) of the memory may be written to, or erased, by each of the controller networks.

Additionally, according to a second embodiment, the invention provides a method for medical image segmentation, comprising:

providing a plurality of patches of an N-dimensional medical image to be segmented;

sequentially receiving, by a first trained neural network acting as a first controller network, input data representing each of the plurality of patches in a first patch sequence, sequentially generating and outputting, by the first controller network, data indicative of a respective first patch segmentation mask candidate for each of the plurality of patches;

sequentially receiving, by a second trained neural network acting as a second controller network, input data representing each of the plurality of patches in a second patch sequence, sequentially generating and outputting, by the second controller network, data indicative of a respective second patch segmentation mask candidate for each of the plurality of patches;

wherein the second patch sequence is different from the first patch sequence;

writing, by the first controller network, data relating to a state of the first controller network to a memory for at least the second controller network;

reading, by the second controller network, at least part of the data written by the first controller network from the memory;

utilizing, by the second controller network, the read data when generating the data indicative of at least one of the second patch segmentation mask candidates; and generating, based on the data indicative of the first and second patch segmentation mask candidates, a final image segmentation mask for segmenting the N-dimensional medical image.

As will be discussed in more detail in the following, the providing of the plurality of patches may comprise encoding raw input intensity patches into more abstract representations, e.g. using a fully convolutional neural network as an encoder module. Similarly, the generating of the final image segmentation mask may comprise decoding abstract representations into image segmentation mask candidates, e.g. using a fully convolutional neural network as a decoder module.

Moreover, according to a third embodiment, the invention provides a computer-readable data storage medium comprising executable program code configured to, when executed, perform a method according to the second embodiment of the present invention.

According to a fourth embodiment, the invention provides a computer program product comprising executable program code configured to, when executed, perform a method according to the second embodiment of the present invention.

Advantages of the Embodiments

The first and the second controller networks work along different patch sequences through the plurality of patches of the N-dimensional medical image. Each controller network naturally utilizes information about the previously processed patch for the processing of the presently processed patch, simply by data propagation along the respective trained neural network, wherein each layer of level of the trained neural network may correspond to the processing of one particular patch.

In this way, each controller network utilizes knowledge about all of the previously processed patches. Providing at least two controller networks that work along different patch sequences means that at each point in time, possibly barring the end of the procedure, the two controllers would ordinarily work with different knowledge about the global context of the patches. Each controller network has information about the foregoing patches (i.e. the patches previously processed by the same controller) but has, so far, no information about the following patches (i.e. the patches to be processed in the following by the same controller).

One of the main ideas of an embodiment of the present invention has been to realize that, by using two controller networks, each controller network may provide to the other controller network information about its following patches. This is achieved by the shared memory to which both (or all in the case of more than two) controller networks are able to write data, and from which both (or all in the case of more than two) controller networks are able to retrieve data.

As an intuitive example, the second controller may already have correctly identified an organ in a patch in its patch sequence as a human heart, and may have written data representing a corresponding segmentation mask candidate into the memory. The first controller could then, when processing a patch e.g. in the upper left of the N-dimensional medical image that comprises an unclear portion that resembles a human heart, have learned to read corresponding data from the shared memory and thus obtain valuable and relevant context data. In the present example, the context data would strongly suggest that the first controller should not segment the unclear portion as a human heart, even though the first controller network itself would only much later process the patch which actually comprises the human heart.

Put in yet again different words: the first and second controller networks share an external memory which gives them access to the context of the N-dimensional medical image seen by other controller networks to better capture global information (i.e. information relating to a plurality of patches or even to the N-dimensional medical image in its entirety) which can lead to more robust predictions by the system.

It has been found that advantageously the first and the second controller network are realized as recurrent neural networks such as LSTM (long short-time memory) networks, GRU (gated recurrent unit) networks and the like. However, also other neural network architectures may be used for the first and the second controller networks such as feed-forward neural networks or the like.

Further advantages and preferred embodiments will be evident from the dependent claims as well as from the description, taking into account also the attaches figures.

In the following, a plurality of different neural network will be introduced in the context of advantageous embodiments and optional modifications. For the sake of intelligibility, the neural networks are numbered (third, fourth, . . . , xth neural network). This, however, does not imply any order or that, for an xth neural network to be present, first an (x−1)th neural network has to be present.

In some advantageous embodiments, the second controller network is further configured to write data relating to a state of the second controller network to the memory, e.g. as context data, and the first controller network is configured to read at least part of the data written by the second controller network from the memory and to utilize the read data when generating the data indicative of at least one of the first patch segmentation mask candidates.

In other words, not only the first controller network may write data to the shared memory that is useful for the second controller but also vice versa. This greatly improves the performance of both of the controller networks.

In some advantageous embodiments, the second patch sequence equals the reversed first patch sequence. In other words, if the first patch sequence $s_1$ is characterized by the ordered set of $s_1=\{p_1, p_2, p_3, \ldots, p_{M-2}, p_{M-1}, p_M\}$, wherein $p_i$ designates a patch of a plurality of M patches, then the second patch sequence $s_2$ may be characterized by the ordered set of $s_2=\{p_M, p_{M-1}, p_{M-2}, \ldots, p_3, p_2, p_1\}$.

In other advantageous embodiments, the first and the second patch sequence may differ in other ways, e.g. the first patch sequence may indicate that patches are processed in subsequent rows ("horizontal scanning"), whereas the second patch sequence indicates that patches are processed in subsequent columns ("vertical scanning").

The system may also comprise more than two controller networks, each controller network provided with a difference patch sequence. The controller networks may be divided into disjunct pairs, and a shared memory may be provided for each pair of controller networks, wherein each controller network may write context data to its provided shared memory and read context data written by the other controller network of the same pair into the same memory.

Alternatively, there may be a single shared memory shared by all of the controller networks, wherein each controller network is able to write context data to the memory, and each of the controller networks is able to retrieve data written by each of the controller networks from the memory.

For example, the first patch sequence may indicate that patches are processed in subsequent rows from the top down, the second patch sequence may indicate that patches are processed in subsequent rows from the bottom up, a third patch sequence may indicate that patches are processed in subsequent columns from left to right, and a fourth patch sequence may indicate that patches are processed in subsequent rows columns from right to left.

In some advantageous embodiments, the computing device is configured to implement at least one trained third neural network as a first memory write head usable by the first controller network for writing to the memory. The at least one first memory write head may be implemented as at least one single-layer or multi-layer neural network. Preferably, each of the at least one first memory write heads comprises a write key sub-module, an erase sub-module and/or an add sub-module, each preferably implemented as a trained neural network, in particular as a trained single layer neural network. More preferably, the write key sub-module neural network is provided with a rectified linear (ReLU) activation unit and/or the erase sub-module is provided with a sigmoid activation unit and/or the add sub-module is provided with a tank activation unit.

Preferably, the at least one first write head is implemented using only a differentiable transformations of a vector, often designated ct, representing states of the first controller network. In this way, the at least one first write head may be easily trained together with other neural networks as the differentiability allows for efficient backpropagation during training. The transformations may be linear or non-linear transformations.

In some advantageous embodiments, the computing device is configured to implement at least one trained fourth neural network as a second memory write head usable by the second controller network for writing to the memory. The at least one second memory write head may be implemented as at least one single-layer or multi-layer neural network. Preferably, each of the at least one second memory write heads comprises a write key sub-module, an erase sub-module and an add sub-module, each preferably implemented as a trained neural network, in particular as a trained single layer neural network. More preferably, the write key sub-module neural network is provided with a rectified linear (ReLU) activation unit and/or the erase sub-module is provided with a sigmoid activation unit and/or the add sub-module is provided with a tank activation unit.

Preferably, the at least one second write head is implemented as a differentiable transformation of vectors representing states of the second controller network. In this way, the at least one second write head may be easily trained together with other neural networks as the differentiability allows for efficient backpropagation during training. The transformations may be linear or non-linear transformations.

In some advantageous embodiments, a plurality of first memory read heads and/or a plurality of second memory read heads is provided for the respective controller network (or for any or each of a plurality of three or more controller networks). This allows the controller networks, respectively, to write to a plurality of locations and/or using a plurality of writing strategies at the same time. The neural networks realizing the plurality of the respective memory write heads may be initially set up in the same way but may be provided with different initialization values before training. Thus, during training, the individual memory write heads may learn different advantageous writing strategies.

In some advantageous embodiments, the computing device is configured to implement at least one trained fifth neural network as a first memory read head usable by the first controller network for reading from the memory. The at least one first memory read head may be implemented as a multi-layer neural network. Preferably, the at least one first memory read head is implemented as a single layer neural network. Advantageously, a rectified linear unit (ReLU) is used as an activation unit of the third neural network.

Preferably, the at least one first memory read head is implemented as a differentiable transformation of context vectors representing the context data within the memory. In this way, the at least one read head may be easily trained together with other neural networks as the differentiability allows for efficient backpropagation during training.

In some advantageous embodiments, the computing device is configured to implement at least one trained sixth neural network as a second memory read head usable by the second controller network for reading from the memory. The at least one second memory read head may be implemented as a multi-layer neural network. Preferably, the at least one second memory read head is implemented as a single layer neural network. Advantageously, a rectified linear unit (ReLU) is used as an activation unit of the fourth neural network.

Preferably, the at least one second memory read head is implemented as a differentiable transformation of context vectors representing the context data within the memory, with the advantages as described in the foregoing.

In some advantageous embodiments, a plurality of first memory read heads and/or a plurality of second memory read heads is provided for the first or second controller network, respectively (or for any or each of a plurality of three or more controller networks). This allows the controller networks, respectively, to read from a plurality of locations and/or using a plurality of reading strategies at the same time. The neural networks realizing the plurality of the respective read heads may be initially set up in the same way but may be provided with different initialization values before training. Thus, during training, the individual read heads may learn different advantageous reading strategies.

In some advantageous embodiments, the system comprises a database shared by at least the first and the second controller network (and, if applicable, by further controller networks provided in the system).

The database comprises key vectors linked to (or, in other words, labelled with) a plurality of datasets. The computing device is configured to implement at least one trained seventh neural network as at least one first database read head usable by the first controller network and/or at least one trained eighth neural network as at least one second database read head usable by the second controller network.

Training of the first and second controller network is advantageously performed in one and the same process as training of the various write and read heads. Thus, the write and read heads are trained to optimally write or retrieve, respectively, data into or from, respectively, the memory or the database, respectively.

The database may be saved locally, e.g. in a second memory or in a part of the original memory that is not accessible by the memory read heads. The database may also be saved in distributed form or in a cloud. The database may be implemented as a matrix, an SQL database, an apache-hadoop based database or in other ways.

The at least one first and/or second database read head (and/or any additionally provided database read heads e.g. for additional controller networks), respectively, are configured (specifically: trained) and usable to retrieve, based on the key vectors, data based on at least one of the plurality of datasets from the database. The database may also comprise previously determined patch segmentation mask candidates that may be retrieved and output directly as first or second patch segmentation candidates, respectively.

For example, the database may comprise, as the datasets, features of a neural network, e.g. features of a deep convolutional neural network, or displacement vectors (see e.g. "Milletari et al." cited in the foregoing, the entire contents of which are hereby incorporated herein by reference) or any other relevant sets of information that may help with the segmentation process.

Preferably, none of the controller networks is provided with a write head for writing to the database. Instead, the database preferably comprises only external knowledge such as atlas images preselected e.g. by a diagnostic expert. The database may be available both during training and testing of any or, preferably, of all of the neural networks of the system. Advantageously, the database can be arbitrarily updated with new datasets, e.g. new atlases.

In some advantageous embodiments, the computing device is configured to implement an encoder module configured to receive the patches from the input module and to generate the input data representing each of the plurality of patches for the first and the second controller network.

Preferably, the computing device is configured to implement a trained ninth neural network as the encoder module.

The ninth neural network is, more preferably, implemented as a convolutional neural network which creates feature channels from the raw image data. Some channel may be related to different colours or greyscales, to the presence of edges, of certain textures, to Dixon channels, channels representing fat tissue and so on. In this way, the available computing power may be more efficiently used.

In some advantageous embodiments, the computing device is further configured to generate, using the data indicative of the first patch segmentation mask candidates, data indicative of a first image segmentation mask candidate, and to generate, using the data indicative of the second patch segmentation mask candidates, data indicative of a second image segmentation mask candidate, and to generate data indicative of a final image segmentation mask based on the first and the second image segmentation mask candidates.

The system further may comprise a decoder module configured to generate, from the data indicative of the final image segmentation mask, the final image segmentation mask for segmenting the N-dimensional medical image.

In some advantageous embodiments, the computing device is configured to implement a trained tenth neural network as the decoder module.

In some advantageous embodiments, the computing device is further configured to implement a trained eleventh neural network as a fusion module, wherein the fusion module is configured to generate the data indicative of the final image segmentation mask based on the data indicative of the first and the second image segmentation mask candidates. The data indicative of the final image segmentation mask may be decoded, e.g. by the decoder module, to generate the image segmentation mask.

In some advantageous embodiments, all of the neural networks of the system that are employed are configured to be differentiable. As described in the foregoing, in this way, efficient backpropagation and therefore efficient training and testing may be realized.

In some advantageous embodiments of the method according to the second embodiment of the present invention, the method further comprises:
  writing, by the second controller network, data relating to a state of the second controller network to a memory as context data;
  reading, by the first controller network, at least part of the context data from the memory;
  utilizing, by the first controller network, the read data when generating the data indicative of at least one of the first patch segmentation mask candidates.

In this way, both the first and the second controller network are able to receive long-range context data from the respective other controller network and will therefore process the patches with improved efficiency and accuracy.

Although specific embodiments have been illustrated and described herein, it will be appreciated by those of ordinary skill in the art that a variety of alternate and/or equivalent implementations may be substituted for the specific embodiments shown and described without departing from the scope of the present invention. Generally, this application is intended to cover any adaptations or variations of the specific embodiments discussed herein.

FIG. 1 schematically illustrates a procedure of patchwise processing of an N-dimensional medical image 1 that has been divided into N=12 individual patches 2-1, 2-2, . . . , 2-12 (collectively designated as **2-*i*) to generate an N-dimensional image segmentation mask 3 using first a controller network 10 that is implemented as a recurrent neural network. The first controller network 10** may, as has been described in the foregoing, also be realized as another type of a neural network.

Since there are N=12 patches, the patch-wise processing will take N=12 steps at twelve subsequent points in time, t=1, t=2, . . . , t=N=12, from which steps t=6, t=7 and t=12 are sketched as examples in FIG. 1. Although the patches **2-*i*** are shown as touching but disjunct, it will be understood that, as discussed in the foregoing, the patches may also be provided such that they overlap each other in some way, which is advantageous for putting the individual patch segmentation masks together to form the final image segmentation mask.

In each step, input data **11-*i* are input into the first controller network 10** which is in a hidden state that comprises information about the previous steps (except at t=1).

At t=6, for example, the controller network 10 will start in a hidden state comprising information about the five previously processed patches 2-1, . . . , 2-5. At each step t, the first controller network 10 receives input data **11-*i* representing the patch 2-*i* to be processed next. Accordingly, at step t=6, the first controller network 10 receives input data 11-6 representing the sixth patch 2-6. In addition, the first controller network 10 may retrieve data from a memory 200 and, optionally, data from a database 300**, both of which will be described in more detail with respect to the following figures.

In the upper line of FIG. 1, progress in determining the final image segmentation mask for the left kidney 4 is depicted. At step t=6, processing of patches 2-3 and 2-4, which contain parts of the N-dimensional medical image that represent parts of the left kidney 4, has previously led to parts of the left kidney 4 be contained in the image segmentation mask 3 for the left kidney 4. As is illustrated schematically in FIG. 1, at the end at step t=12, additional data, presumably from the processing of patches 2-7 and 2-8, will have led to an accurate representation of the left kidney 4 in the final image segmentation mask 3 for the left kidney 4, as shown in the upper right of FIG. 1.

Roughly speaking, each processing step t=i produces output data **13-*i* that may add to the final image segmentation mask 3. Usually, the output data 13-*i* will represent a first patch segmentation mask candidate from the first controller network 10 for patch 2-*i* that has to be aggregated with all the other patch segmentation mask candidates to form the final image segmentation mask 3**.

Figure 2:
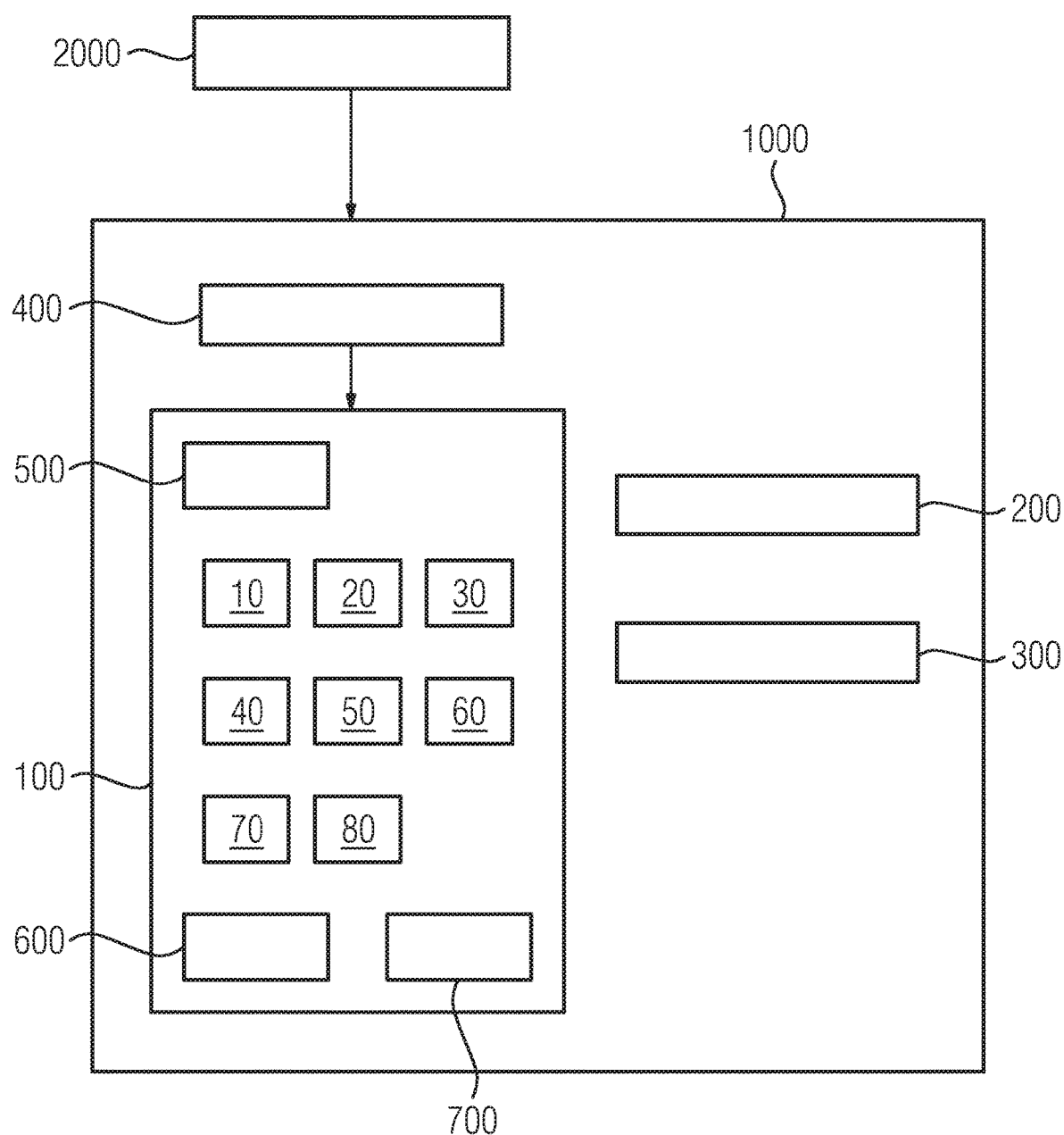
FIG. 2 shows a schematic block diagram illustrating a system for medical image segmentation according to an embodiment of the first embodiment of the present invention.

FIG. 2 shows a schematic block diagram illustrating a system 1000 for medical image segmentation according to an embodiment of the first embodiment of the present invention. The system 1000 comprises a computing device 100, and a memory 200. Optionally, the system 1000 may also comprise a database 300.

The system 1000 may receive data signals from a medical imaging device 2000 such as an MRI or an X-ray machine. The medical imaging device 2000 may, in some embodiments, be a part of the system 1000.

The computing device 100 may be a single processor core or a microprocessor. Preferably, the computing device is an array of processor cores or central processing units (CPUs). More preferably, the computing device is an array of graphical processing units (GPUs). The computing device 100 may also be realized partially or completely by interconnected remote devices such as cloud computing servers.

The computing device 100 is configured to implement a trained first neural network as a first controller network 10 and a trained second neural network as a second controller network 20.

The computing device may be further configured to implement any or all of optional trained neural networks 30 to 80 as will be described in the following.

Figure 3:
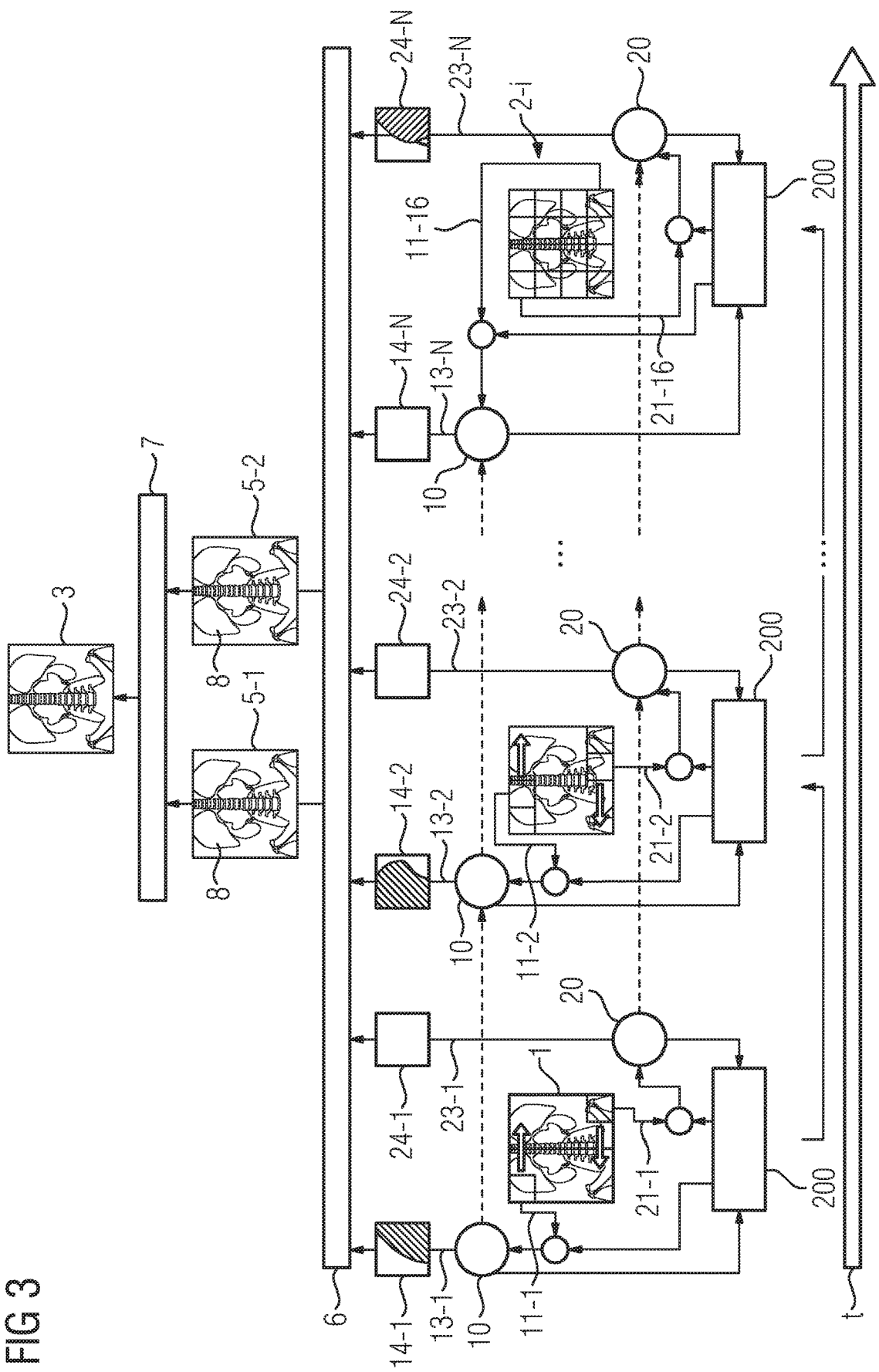
FIG. 3 shows a schematic flow diagram illustrating the function of the system for medical image segmentation according to FIG. 2.

FIG. 3 shows a schematic flow diagram illustrating the function of the system for medical image segmentation according to FIG. 2.

In the lower end, again time steps from 1 to N are indicated. The functioning of the system 1000 will be described using the example of an N-dimensional medical image 1 to be segmented such that the final image segmentation mask indicates the position and extent of the right lung 8 of a patient.

The N-dimensional medical image 1 is, for the present example, divided into 16 patches 2-*i* in a 4×4 grid. It should be understood that any number of patches 2-*i* in any sort of array may be used. As described in the foregoing, the patches 2-*i* may or may not overlap and/or may or may not be of the same size, although patches 2-*i* of the same size are preferred for easier treatment, and patches 2-*i* overlapping at least partially with at least some of their neighbours are preferred for easier aggregation to the final image segmentation mask.

The patches 2-*i* may be provided by an input module 400 of the system 1000, the input module 400 being configured to provide the plurality of patches 2-*i* of the N-dimensional medical image 1 to be segmented. The input module 400 may be implemented by the computing device 100, e.g. as another trained neural network, or it may be provided separately.

For example, a medical imaging device 2000 may produce N-dimensional medical images 1 that are automatically, or on cue by a user, transmitted to the input module 400, wherein the N-dimensional medical images 1 are divided into the patches 2-*i*. The number and arrangement of the patches may be the same for all received N-dimensional medical images 1, or may be automatically determined and set by the input module 400 depending on properties of each individual N-dimensional medical image 1 and/or based on an input of a user.

For example, the user may set a degree of resolution, wherein a comparatively higher set degree of accuracy will lead to the N-dimensional medical image 1 being divided into comparatively more patches, and wherein a comparatively lower set degree of accuracy will lead to the N-dimensional medical image 1 being divided into comparatively less patches.

In case that the input module 400 is realized as another neural network and is implemented by the computing device 100, the input module 400 may have been trained jointly with the other neural networks implemented by the computing device 100 such that the input module 400 is trained to divide each N-dimensional medical image 1 into an optimal number and/or arrangement of patches.

The first controller network 10 is configured and trained to sequentially (i.e. patch-wise) receive input data 11-*i* representing each of the plurality of patches 2-*i* in a first patch 2-*i* sequence s1, and to sequentially generate and output data 13-*i* (i=1 . . . N) indicative of a respective first patch segmentation mask candidate 14-*i* (i=1 . . . N) for each of the plurality of patches 2-*i*.

The second controller network 20 is configured and trained to sequentially (i.e. patch-wise) receive input data 21-*i* representing each of the plurality of patches 2-*i* in a second patch sequence s2, and to sequentially generate and output data 23-*i* (i=1 . . . N) indicative of a respective second patch segmentation mask candidate 24-*i* (i=1 . . . N) for each of the plurality of patches 2-*i*.

The input data 11-*i*, 21-*i* may directly correspond to the raw slices of image data that make up the patches. Alternatively, the computing device 100 may be configured to implement an encoder module 500 configured to receive the patches 2-*i* from the input module 400 and to generate the input data 11-*i*, 21-*i* representing each of the plurality of patches 2-*i* for the first and the second controller network 10, 20. Put in another way, the encoder module 500 encodes the image data that make up the patches into a data format that can be processed by the controller networks 10, 20, in particular into abstract representations of the raw pixels of the input patches 2-*i*.

Preferably, the computing device 100 is configured to implement a trained neural network as the encoder module 500. The neural network is optionally implemented as a convolutional neural network which creates feature channels from the raw image data. Some channel may be related to different colours or greyscales, to Dixon channels, channels representing fat tissue and so on.

For each controller network 10, 20, a corresponding patch sequence s1, s2 is defined. The patch sequence s1, s2 may be preset by a user or may be trained/learned by the neural networks of the system 1000 during training of the system 1000.

Preferably, the second patch sequence s2 equals the reversed first patch sequence s1. In other words, if the first patch sequence $s_1$ is characterized by an ordered set of $s_1=\{2\text{-}1, 2\text{-}2, 2\text{-}3, \ldots, 2\text{-}(N-2), 2\text{-}(N-1), 2\text{-}N\}$, of the plurality of N patches, then the second patch sequence $s_2$ may be characterized by the ordered set of $s_2=\{2\text{-}N, 2\text{-}(N-1), 2\text{-}(N-2), \ldots, 2\text{-}3, 2\text{-}2, 2\text{-}1\}$.

Figure 4:
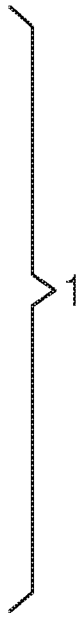
FIG. 4 illustrates a scheme for the designation of the patches as used in the embodiment of FIG. 2.

FIG. 4 illustrates the designation of the patches 2-1, . . . , 2-16 for the presently used example.

The present example uses a first patch sequence s1 which starts in the upper left corner (2-1), proceeds along a horizontal line from left to right (or, in other words, forward along a first linear direction), then moves down (or, in other words, forward along a second linear direction perpendicular to the first linear direction) to the next lower horizontal line (patches 2-5 through 2-8), where it starts again from left to right (forward along the first linear direction) and so on. Thus, the first patch sequence s1 ends with patch 2-16 in the lower right corner.

Accordingly, the second patch sequence s2 starts in the lower right corner (i.e. patch 2-16) and works from right to left (or, in other words, backward along the first linear direction), then moves up (or, in other words, backward along the second linear direction) to the next higher horizontal line (patches 2-9 through 2-12), where it starts again from right to left (backward along the first linear direction) and so on. Thus, the second patch sequence s2 ends with patch 2-1 in the upper left corner.

It will be understood that also other patch sequences may be employed, for example s1={2-1, 2-2, 2-3, 2-4, 2-8, 2-7, 2-6, 2-5, 2-4, 2-9, 2-10, 2-11, 2-12, 2-16, 2-15, 2-14, 2-13} and, correspondingly, s2 in the inverse order.

An example of two different patch sequences s1, s2 which are not each other's inverse is s1={2-1, 2-2, 2-3, 2-4, 2-8, 2-7, 2-6, 2-5, 2-4, 2-9, 2-10, 2-11, 2-12, 2-16, 2-15, 2-14, 2-13} and s2={2-16, 2-15, 2-14, 2-13, 2-9, 2-10, 2-11, 2-12, 2-8, 2-7, 2-6, 2-5, 2-1, 2-2, 2-3, 2-4}.

Patch sequences that are not each other's inverse may be advantageous if, for example, the patch sequences are chosen to follow strategies adapted to the contents of the N-dimensional medical image 1. For example, one patch sequence could roughly follow the patches containing with high probability a human spine so that the controller network processing patches 2-*i* along this patch sequence is able to establish an implicit difference between organs on the left-hand side and organs on the right-hand side.

FIG. 3 illustrates how, at the different time steps from t=1 to t=N, the two controller networks 10, 20 move through the patches 2-*i* according to their respective patch sequences.

FIG. 3 also illustrates that, in each time step t after the first at t=1, the controller networks 10, 20 are not only provided with the features, or hidden state, of the respective controller network 10, 20 from the previous time step (t−1), as indicated by the dashed arrows, but also with additional data from a memory 200 shared by the controller networks 10, 20. That additional data (or: memory read output) may be represented by a vector that is then concatenated with a vector representing the input data 11-$i$, 21-$i$.

As is illustrated in FIG. 3, the memory 200 may be initialized with a starting set of data so that the controller networks 10, 20 are, already in the first time step t=1, able to retrieve data from the memory 200. Alternatively, the memory 200 may be initialized as empty and will only be filled during the operation, or processing, by the controller networks 10, 20.

The interaction between the controller networks 10, 20 and the memory 200 will be explained in the following in more detail also with respect to FIG. 5.

Figure 5:
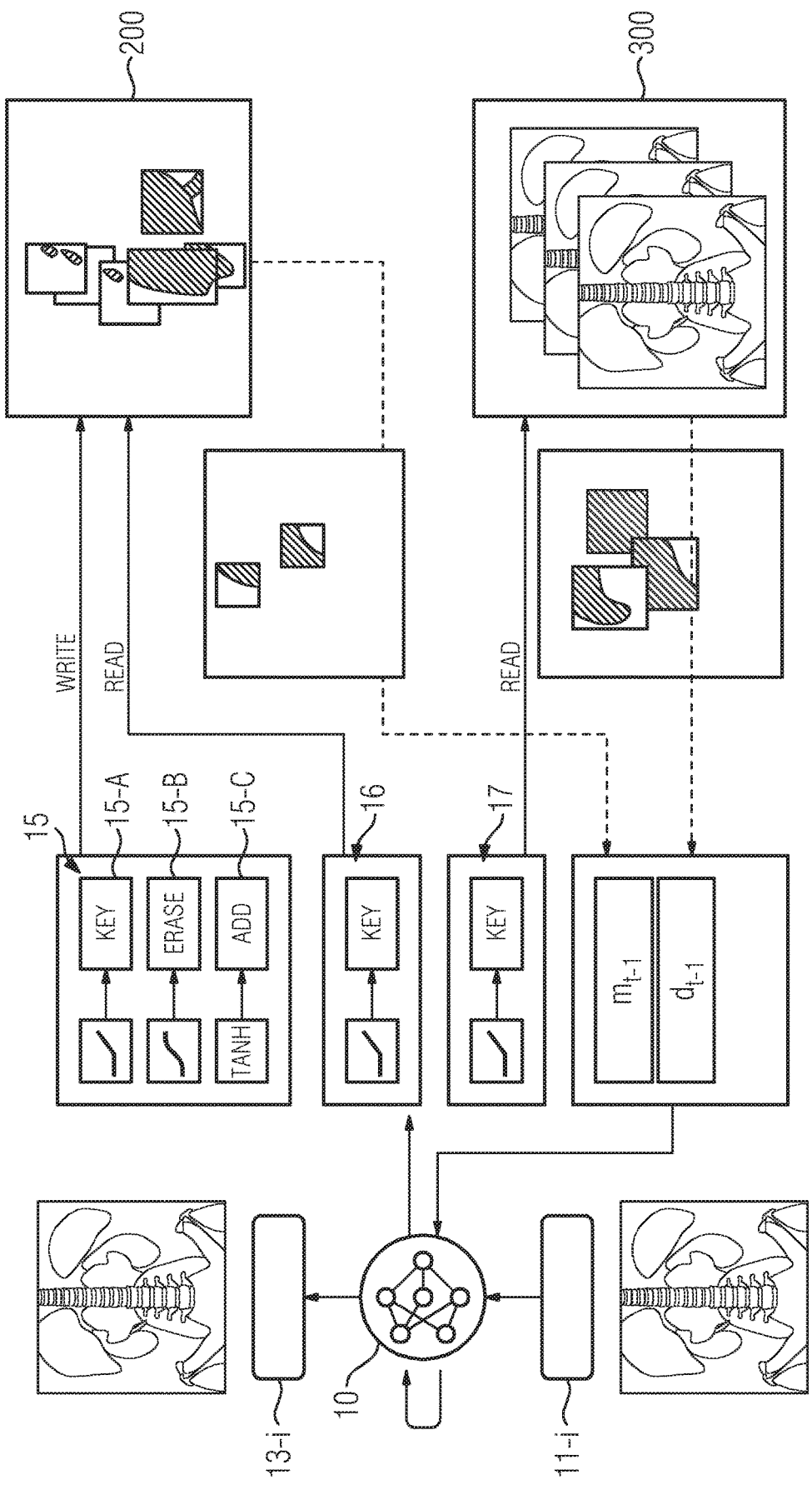
FIG. 5 shows a schematic block diagram further illustrating the function of the system for medical image segmentation according to FIG. 2 and FIG. 3.

FIG. 5 shows a schematic block diagram further illustrating the function of the system 1000 for medical image segmentation according to FIG. 2 and FIG. 3. The following explanation will focus on the first controller network 10. It will be understood that the same explanation equally applies to the second controller network 20, even if at times the second controller network 20 is not explicitly mentioned.

The computing device 100 is configured to implement, for the first controller network 10, at least one memory write head 15 and at least one memory read head 16 (and similarly for the second controller network 20). In FIG. 5, as an example one memory write head 15 and one memory read head 16 are shown. However, it should be understood that both the number of memory read heads 16 and of memory write heads 15 may be higher, with the aforementioned advantages.

The memory write heads 15 and memory read heads 16 of the first controller network 10 may be designated as first memory write heads 15 and first memory read heads 16, respectively, and memory write heads and memory read heads of the second controller network 20 may be designated as second memory write heads and second memory read heads. In the following, for the sake of intelligibility, the description will focus on the first controller network 10 and therefore usually drop the labels "first".

The memory write head 15 is preferably implemented as at least one trained third neural network 30 by the computing device 100. More preferably, as illustrated by way of FIG. 5, each memory write head 15 comprises a write key sub-module 15-A, an erase sub-module 15-B and an add sub-module 15-C, each preferably implemented as a trained neural network, in particular as a trained single layer neural network. Most preferably, the write key sub-module 15-A neural network is provided with a rectified linear (ReLU) activation unit and/or the erase sub-module 15-B neural network is provided with a sigmoid activation unit and/or the add sub-module 15-C neural network is provided with a tanh activation unit, as schematically indicated in FIG. 5.

The write key sub-module 15-A realizes a write key which determines in which locations of the memory 200 data will be added, or, in other words, which values will be updated to which degree. The erase sub-module 15-B realizes an erase vector et which controls whether/which information will be removed from the memory 200. The add sub-module 15-C realizes an add vector (or add gate) at which control whether/which information will be added to the memory 200.

The memory write head 15 preferably interacts with the memory 200 in an addressing scheme based on soft attention (see scientific publication "Graves 2014", the entire contents of which is hereby incorporated herein by reference). This is an efficient way to keep the corresponding architecture differentiable.

The memory write head 15 is preferably configured such that its interaction with the memory 200 is constrained by weights associated with previous observations from the memory 200 (or from the database that will be described in the later). These weights can be derived by combining multiple addressing mechanisms, e.g. content-based, location-based and/or temporal-based addressing, see scientific publication "Graves 2016" cited above, the entire contents of which is hereby incorporated herein by reference. In the following, as one example, memory write heads based only on content-based addressing are described. It will be understood that any or all of the other addressing mechanisms described above may be applied additionally or instead, individually or in any combination thereof.

The memory contents $M_t$ at time step t may thus in particular be updated using the memory contents $M_{t-1}$ at the previous time step (t−1), the identity operation I, the erase vector et, the add vector at and a write memory attention score $p_t^{Mem,w}$, as follows:

$$M_t \leftarrow (M_{t-1}[I-p_t^{Mem}e_t])+p_t^{Mem,w}a_t$$

The write memory attention score $p_t^{Mem,w}$ preferably depends on the memory contents $M_{t-1}$ at time step t−1 and on a memory write key vector $k_t^w$ emitted by the write key sub-module 15-A for time step t. More preferably, the write memory attention score $p_m^{Mem,w}$ is based on a similarity metric $F(k_t^w, M_{t-1}[i])$ which indicates a similarity between the two vectors $k_t^w$ and $M_{t-1}[i]$, wherein $M_{t-1}[i]$ is the i-th row of the matrix $M_{t-1}$. For example, the similarity metric F may comprise, or consist of, an inner product and/or a cosine similarity. The memory write key vector $k_t^w$ may be different for each memory write head.

In especially preferred embodiments, the write memory attention score $p_t^{Mem,w}$ is a vector (more specifically a column vector) defined by each of its components $p_t^{Mem,w}[i]$ being defined as:

$$p_t^{Mem,w}[i] = \frac{\exp(F(k_t^w, M_{t-1}[i]))}{\sum_{j=1}^{L} \exp(F(k_t^w, M_{t-1}[j]))},$$

wherein L designates the number of rows of the matrix $M_{t-1}$, and $M_{t-1}[i]$ is the i-th row of $M_{t-1}$.

Using the memory write heads, the first and second controller network 10, 20 are thus able to write, after being trained, data relating to states of the respective controller network 10, 20 into the memory 200, and to retrieve both data that they themselves have written to the memory 200 as well as data that the respective other controller network 20, 10 has written to the memory.

Since the controller networks 10, 20 process the plurality of patches 2-$i$ according to different patch sequences, this means that the data written by each controller network 10, 20 will provide the respective other controller network 20, 10 with global context information about other patches 2-$i$. In particular when the two patch sequences are each other's reverse, then advantageously each controller network 10, 20 will be able to retrieve data pertaining to its—yet—unprocessed patches 2-$i$. The retrieving process will be described in more detail in the following with respect to the memory write heads.

The first controller network 10 will be able to utilize the retrieved data to generate the output data 13-$i$ indicative of the first patch segmentation candidates 14-$i$. Conversely, the second controller network 20 will be able to utilize the retrieved data to generate data 23-$i$ indicative of the second patch segmentation candidates 24-$i$.

It will be understood that the memory write heads for the second controller network 20 may be provided as described in the foregoing for the memory write head 15 of the first controller network 10. In particular, the memory write heads of the second controller network 20 are preferably implemented as at least one trained fourth neural network 40 by the computing device 100.

The computing device 100 of FIG. 2 is preferably further configured to implement at least one trained fifth neural network 50 as a first memory read head 16 usable by the first controller network 10 for reading from the memory 200. Similarly, the computing device 100 of FIG. 2 is preferably further configured to implement at least one trained sixth neural network 60 as a second memory read head usable by the second controller network 20 for reading from the memory 200. The function of the memory read heads will in the following again be described with respect to the first memory read heads 16.

Not necessarily, but preferably, the memory read heads are implemented as differentiable transformations of context vectors representing the context data (i.e. contents) within the memory 200. Preferably, the at least one first memory read head 16 is implemented as a single layer neural network. Advantageously, a rectified linear unit (ReLU) is used as an activation unit of the third neural network.

The memory read output $m_t$ of the memory read operation at time step t may be described by a weighted sum of the rows $M_t[i]$ of the matrix $M_t$, e.g. by $$m_t = \sum_{i=1}^{L} p_t^{Mem,r}[i] * M_t[i]$$

with a read memory attention score $p_t^{Mem,r}$.

The read memory attention score $p_t^{Mem,r}$ preferably depends on the memory contents $M_t$ at time step t and on a memory read key vector $k_t^{Mem,r}$ generated by the memory read head 15 for the time step t. The memory read key vector $k_t^{Mem,r}$ may be different for each memory read head 16.

More preferably, the read memory attention score $p_t^{Mem,r}$ is based on a similarity metric $F(k_t^{Mem,r}, M_t[i])$ which indicates a similarity between the two vectors $k_t^{Mem,r}$ and $M_t[i]$. For example, the similarity metric F may comprise, or consist of, an inner product and/or a cosine similarity.

In especially preferred embodiments, the read memory attention score $p_t^{Mem,r}$ is a vector (more specifically a column vector) defined by each of its components $p_t^{Mem,r}[i]$ being defined as:

$$p_t^{Mem,r}[i] = \frac{\exp(F(k_t^{Mem,r}, M_t[i]))}{\sum_{j=1}^{L} \exp(F(k_t^{Mem,r}, M_t[j]))},$$

wherein L designates the number of rows of the matrix $M_t$, and $M_t[i]$ is the i-th row of $M_t$.

At each step t, the controller networks 10, 20 will receive not only input data 11-$i$ representing the patch 2-$i$ to be processed in the time step t but also a memory read output $m_t$ of the memory read operation by each memory read head 16 of the respective controller network 10, 20.

In that case, the controller networks 10, 20 may be realized as LSTM (long short-time memory) networks, and the system 1000 may be designated as a Single Feedback Recurrent Memory Network (SFRMN). Another abstract way to portray the updating of the output and internal state of the controller network is:

$$[h_t, c_t] = \text{LSTM}([x_t, m_{t-1}]h_{t-1}, c_{t-1}),$$

wherein LSTM indicates the LSTM properties of the controller network, $x_t$ is the embedding of the input (representing, or based on, the patches 2-$i$, e.g. the output of a convolutional neural network), ht is an output of the LSTM network, $c_t$ is a memory cell of the LSTM network, $m_{t-1}$ is the previously memory read output of the read operation and $[x_t, m_{t-1}]$ denotes the concatenation of two vectors as input for the controller network that acts as an LSTM network.

With respect to FIG. 5, also the optional use of an optional database 300 is described. Many possible variants and modifications have already been described in the foregoing when the advantages and dependent claims of the present invention were discussed.

The database may comprise key vectors linked to a plurality of datasets. The computing 100 device is configured to implement at least one trained seventh neural network 70 as at least one first database read head 17 usable by the first controller network 10. Similarly, the computing device 100 is configured to implement at least one trained eighth neural network 80 as at least one second database read head usable by the second controller network 20.

The function of the database read heads will in the following again be described with respect to the first database read heads 17. As in the case of the memory read heads, providing a plurality of database read heads allows the controller networks 10, 20 to read from multiple locations and/or according to multiple reading strategies simultaneously, i.e. within one time step t.

The database 300 may be saved locally, e.g. in a second memory or in a part of the original memory 200 that is not accessible by the memory read heads. The database 300 may also be saved in distributed form or in a cloud. The database 300 may be implemented as a matrix, an SQL database, an apache-hadoop based database or in other ways known in the art.

The at least one database read head 17 is preferably configured (specifically: trained) and usable to retrieve, based on the key vectors, data based on at least one of the plurality of datasets from the database 300. The database 300 may also comprise previously determined patch segmentation mask candidates that may be retrieved and output directly as first or second patch segmentation candidates, respectively.

For example, the database may comprise, as the datasets linked to the key vectors, or alternatively as both dataset and key vectors, features of a neural network, e.g. features of a deep convolutional neural network, or displacement vectors (see e.g. Milletari et al. cited in the foregoing, the entire contents of which are hereby incorporated herein by reference) or any other relevant sets of information that may help with the segmentation process.

Preferably, none of the controller networks 10, 20 is provided with a write head capable of writing to the database. Instead, the database 300 preferably comprises only external knowledge such as atlas images preselected e.g. by a diagnostic expert. The database 300 may be available both during training and testing of any or, preferably, of all of the neural networks of the system. Advantageously, the database 300 can be arbitrarily updated with new datasets, e.g. new atlases.

As has been discussed in the foregoing, several addressing mechanisms may be used (content-based, location-based and/or temporal-based). In the following, again only content-based addressing will be described as one possible embodiment.

The database read head may provide a database read output $d_t$
at time step t, defined by a weighted sum of the rows D[i] of the matrix D, e.g. by $$d_t = \sum_{i=1}^{K} p_t^{Db}[i] * D[i]$$

with a database attention score $p_t^{Db}$.

The database attention score $p_t^{Db}$ preferably depends on the database contents D and on the current state of the first controller network 10, and/or on a database read key vector $k_t^{Db,r}$ generated by the database read head 17 for time step t. The database read key vector $k_t^{Db,r}$ may be different for each individual database read head 17.

More preferably, the memory attention score $p_t^{Db}$ is based on a similarity metric $F(k_t^{Db,r}, D[i])$ which indicates a similarity between the two vectors $k_t^{Db,r}$ and D[i], wherein D[i] is a row vector of the matrix D. For example, the similarity metric F may comprise, or consist of, an inner product and/or a cosine similarity.

In especially preferred embodiments, the database attention score $p_t^{Db}$ is a vector (more specifically a column vector) defined by each of its components $p_t^{Db}[i]$ being defined as:

$$p_t^{Db}[i] = \frac{\exp(F(k_t^{Db,r}, D[i]))}{\sum_{j=1}^{K} \exp(F(k_t^{Db,r}, D[j]))}$$

wherein K designates the number of rows of the matrix D, and D[i] is the i-th row of D.

When a database 300 is used as part of the system 1000, then in advantageous embodiments at each step t the controller networks 10, 20 will receive not only input data 11-$i$ representing the patch 2-$i$ to be processed in the time step t and also the memory read output $m_t$ of the memory read operation but also the database read output $d_t$ of the database read operation performed by the database read heads 17.

As the database read output $d_t$ will modify the state of the controller networks 10, 20, this means that in some embodiments the data written to the memory 200 by the memory write heads of the controller networks 10, 20 is at least partially dependent on the contents of the database 300. This allows storing highly relevant, useful and/or efficient data from the database in its context regarding the present N-dimensional medical image 1 within the memory 200 which may improve the image segmentation process.

The controller networks 10, 20 may be designated as Double Feedback Recurrent Memory Networks (DFRMN). Another abstract way to portray the updating of the output and the internal state of the controller network when utilizing the database 300 in some preferred embodiments is:

$$[h_t, c_t] = \text{LSTM}([x_t, m_{t-1}, d_{t-1}], h_{t-1}, c_{t-1}),$$

wherein $x_t$ is the embedding of the input (representing, or based on, the patches 2-$i$, e.g. the output of a convolutional neural network), $h_t$ is an output of the LSTM network, $c_t$ is a memory cell of the LSTM network, $m_{t-1}$ is the previous memory read output of the read operation, $d_{t-1}$ is the previous database read output of the read operation and $[x_t, m_{t-1}, d_{t-1}]$ denotes the concatenation of three vectors as input for the controller network that acts as an LSTM network.

The place of the LSTM network in the foregoing, both in the SFRMN or in the DFRMN, may be taken by a feed forward controller or a GRU and the like.

The computing device 100 is further configured to generate, using the output data 13-$i$ indicative of the first patch segmentation mask candidates 14-$i$, data indicative of a first image segmentation mask candidate 5-1. The first image segmentation mask candidate 5-1 is a candidate, output from the first controller network 10, for the final image segmentation mask 3 of the N-dimensional medical image 1.

The computing device 100 is further configured to generate, using the output data 23-$i$ indicative of the second patch segmentation mask candidates 14-$i$, data indicative of a second image segmentation mask candidate 5-2. The second image segmentation mask candidate 5-2 is another candidate, output from the second controller network 20, for the final image segmentation mask 3 of the N-dimensional medical image 1.

The first and the second image segmentation mask candidates 5-1, 5-2 (and any or all additional image i-th image segmentation mask candidates from possible further controller networks), or data representing them, may then be output separately. Preferably, however, they will be used to generate data indicative of the final image segmentation mask 3. This process may also be termed as fusion 7 and will be described later.

In some embodiments, when more than one object (e.g. organ) is to be identified in the N-dimensional medical image 1, each controller network 10, 20 will learn the segmentation for all of the objects. Due to the training and the different initialization values, each controller network 10, 20 will be trained to develop a different strategy to incorporate spatial dependencies in a specific order, even though all controller networks 10, 20 perform the same segmentation masks.

In other embodiments, there may be provided a pair of a first and a second controller network 10, 20 for each object (e.g. organ) to be identified in the N-dimensional medical image 1. In such embodiments, Q+1 output channels, each representing a mask for a specific object (e.g. organ) may be provided, wherein Q is the number of object classes (e.g. organ classes), and the "+1" is added for the background.

The system 1000 may further comprise a decoder module 600 configured to generate, based on the data indicative of the final image segmentation mask 3, the final image segmentation mask 3 for segmenting the N-dimensional medical image.

Preferably, the computing device 100 is further configured to implement a trained tenth neural network as the decoder module 600.

The fusion 7 of the first and second (and/or additional) image segmentation candidates, or of data representing them, to form the data indicating the final image segmentation mask 3, may be performed by a fusion module 700 of the system 1000. The fusion module 700 may be configured to employ any known fusion technique such as addition, concatenation, averaging, majority voting, or "STAPLE", see abovecited research paper by "Iglesias et al.", the entire contents of which is hereby incorporated herein by reference.

In some embodiments, the computing device 100 is configured to implement a trained eleventh neural network as the fusion module 700. Such a fusion module 700 may then be trained, preferably together with the other neural networks implemented by the computing device 100, in order to learn how to fuse the image segmentation candidates (or the data representing them) using, e.g., deep neural networks. Such a neural network can be extended with its own external memory and corresponding read and/or write heads, in analogy to what has been described in the foregoing with respect to the memory 200 and the memory write and read heads 15, 16.

In order to form the first image segmentation mask candidate 5-1 from the output data 13-$i$ representing the first patch segmentation candidates 14-$i$, the output data 13-$i$ may be decoded and/or aggregated. In other words, in an aggregation step or aggregation stage 6, all the first patch segmentation masks 14-$i$ generated by the first controller network 10 are aggregated over the full image domain of the N-dimensional medical image 1.

Also the aggregation stage 6 may be performed by a trained neural network implemented by the computing device 100, in particular by a deep neural network. Alternatively or additionally, methods like addition, averaging and/or concatenation may be employed in the aggregation stage 6.

It is preferred that all of the neural networks described in the foregoing are configured to be differentiable such that they may form an interrelated system of networks (or, in other words, a larger, more complex network) that in itself is completely differentiable such that all of the individual neural networks may be trained simultaneously with the same data. This is one way to provide the system 1000 to provide a computing device 100 and at least the memory 200 (together with any chosen optional components described in the foregoing), to set up the chosen neural networks according to the chosen embodiment, and to then train all of the neural networks simultaneously using the same training data to obtain, for all of the implemented neural networks, trained neural networks.

In some embodiments, after decoding the output data 13-$i$ and then aggregating the first patch segmentation mask candidates 14-$i$ to the first image segmentation mask candidate 5-1, and after decoding the output data 23-$i$ and then aggregating the second patch segmentation mask candidates 24-$i$ to the second image segmentation mask candidate 5-2, the first and second image segmentation mask candidates 5-1, 5-2 are fused to the final segmentation mask 3. This process may be labelled as "late fusion".

In other embodiments, the first and the second patch segmentation mask candidate 14-$i$, 24-$i$ for each patch 2-$i$ may be fused in a fusion step and then decoded to generate a final patch segmentation mask for each patch 2-$i$, and the final patch segmentation masks may then afterwards, in an aggregation step, be aggregated to the final image segmentation mask. This process may be labelled as "early fusion".

Figure 6:
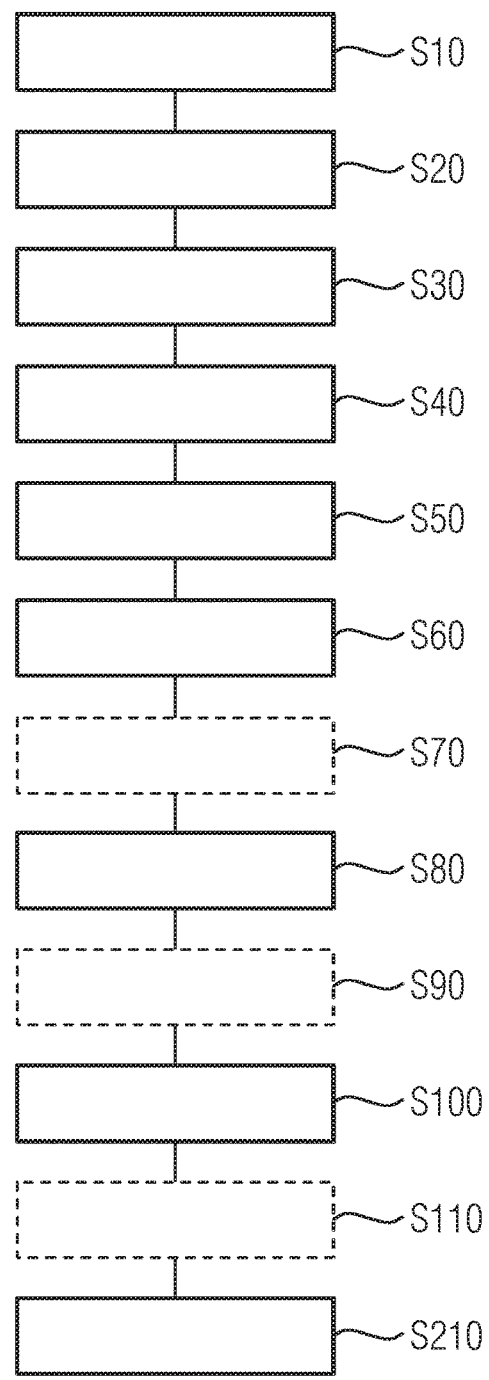
FIG. 6 shows a flow diagram illustrating a method for medical image segmentation according to the second embodiment of the present invention.

FIG. 6 shows a flow diagram illustrating a method for medical image segmentation according to the second embodiment of the present invention.

The method according to FIG. 6 may be performed using the system 1000 as described in the foregoing, and the system 1000 as described in the foregoing may be configured to perform the method according to FIG. 6. Accordingly, the method according to FIG. 6 may be modified, adapted and realized according to any of the embodiments, variants and options described with respect to the system 1000 and vice versa.

The naming and numbering of the steps in the foregoing does not necessarily imply a chronological order, if not otherwise indicated or evident from the content and context. Rather, the step are named and numbered primarily for easier intelligibility.

In at least one step S10 of the method, a plurality of patches of an N-dimensional medical image to be segmented is provided, e.g. as has been described with respect to the input module 400 of the system 1000.

In at least one step S20 a first trained neural network acting as a first controller network 10 sequentially receives input data 11-$i$ representing each of the plurality of patches 2-$i$ in a first patch sequence s1, e.g. as has been described with respect to the system 1000, especially with regard to FIG. 3.

In at least one step S30 a second trained neural network acting as a second controller network 20 sequentially receives input data 21-$i$ representing each of the plurality of patches 2-$i$ in a second patch sequence s2, e.g. as has been described with respect to the system 1000, especially with regard to FIG. 3.

The second patch sequence s2 is different from the first patch sequence s1 and is preferably the reverse of the first patch sequence s1, as has been described in the foregoing in detail.

In at least one step S40, the first controller network 10 sequentially generates and outputs data 13-$i$ indicative of a respective first patch segmentation mask candidate 14-$i$ for each of the plurality of patches 2-$i$.

In at least one step S50, the second controller network 20 sequentially generates and outputs data 23-$i$ indicative of a respective second patch segmentation mask candidate 24-$i$ for each of the plurality of patches 2-$i$.

In at least one step S60, the first controller network 10 writes data relating to a state of the first controller network 10 to a memory 200, e.g. as context data, for at least the second controller network 20, preferably as has been described with respect to the first memory read head 15 in the foregoing.

In at least one optional step S70, the second controller network 20 writes data relating to a state of the second controller network 20 to the memory 200, e.g. as context data, for at least the first controller network 10, preferably as has been described with respect to the first memory read head 15 in the foregoing.

In at least one step S80, the second controller network 20 reads (or, put differently, retrieves) at least part of the data written by the first controller network 10 from the memory 200, preferably as has been described with respect to the first memory read head 16 in the foregoing. It should be understood that in some individual time steps t the second controller network 20 may not read anything at all from the memory 200, or may only read data previously put there by the second controller network 20 itself, and vice versa. This depends of course on how the controller networks 10, 20 have been trained and initialized, on the N-dimensional medical image 1 to be segmented and so on.

In an optional step S90, the first controller network 10 reads at least part of the context data written by the second controller network 20 from the memory 200, preferably as has been described with respect to the first memory read head 16 in the foregoing.

In at least one step S100, the second controller network 20 utilizes the read data when generating the data 23-$i$ indicative of at least one of the second patch segmentation mask candidates 24-$i$.

In at least one optional step S110, the first controller network 10 utilizes the read data when generating the data 13-$i$ indicative of at least one of the first patch segmentation mask candidates 14-$i$.

In at least one step S120, a final image segmentation mask 3 for segmenting the N-dimensional medical image 1 is generated based on the data indicative of the first and second patch segmentation mask candidates.

Figure 7:
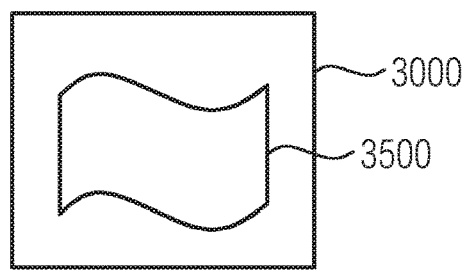
FIG. 7 shows a schematic block diagram illustrating a computer-readable storage medium according to a third embodiment of the present invention as well as a computer program product according to a fourth embodiment of the present invention.

FIG. 7 shows a schematic block diagram illustrating a computer-readable storage medium 3000 according to a third embodiment of the present invention. The storage medium 3000 comprises executable program code 3500 configured to, when executed, perform a method according to the second embodiment of the present invention, in particular the method according to FIG. 6. The computer-readable storage medium may, in particular, be any kind of semiconductor memory, a DVD, a Blu-Ray disc and the like.

FIG. 7 may also be interpreted as illustrating a computer program product according to a fourth embodiment of the present invention. The object labelled with reference sign "3000" may be interpreted as illustrating the computer program product, and the object labelled with the reference sign "3500" may be interpreted as illustrating executable program code configured to, when executed, perform a method according to the second embodiment of the present invention.

In the foregoing detailed description, various features are grouped together in one or more examples or examples with the purpose of streamlining the disclosure. It is to be understood that the above description is intended to be illustrative, and not restrictive. It is intended to cover all alternatives, modifications and equivalents. Many other examples will be apparent to one skilled in the art upon reviewing the above specification.

LIST OF REFERENCE SIGNS

1 N-dimensional medical image
2-$i$ patches
3 final image segmentation mask
4 left kidney
5-1 first image segmentation mask candidate
5-2 second image segmentation mask candidate
6 aggregation stage
7 fusion
8 left lung
10 first controller network
11-$i$ input data
13-$i$ output data
14-$i$ first segmentation mask candidate
15 first memory write head
15-A write key sub-module
15-B erase sub-module
15-C add sub-module
16 first memory read key
17 first database read head
20 second controller network
21-$i$ input data
23-$i$ output data
24-$i$ second segmentation mask candidate
30 trained third neural network
40 trained fourth neural network
50 trained fifth neural network
60 trained sixth neural network
70 trained seventh neural network
80 trained eighth neural network
100 computing device
200 memory
300 database
400 input module
500 encoder module
600 decoder module
700 fusion module
1000 system
2000 medical imaging device
3000 computer-readable storage medium
3500 executable program code

What is claimed is:

1. A system for medical image segmentation, comprising:
an input module, configured to provide a plurality of patches of an N-dimensional medical image to be segmented;
a computing device, configured to implement a trained first neural network as a first controller network and a trained second neural network as a second controller network,
wherein the first controller network is configured to sequentially receive input data representing each of the plurality of patches in a first patch sequence, and to sequentially generate and output data indicative of a respective first patch segmentation mask candidate for each of the plurality of patches,
wherein the second controller network is configured to sequentially receive input data representing each of the plurality of patches which are the same, in a second patch sequence, and to sequentially generate and output data indicative of a respective second patch segmentation mask candidate for each of the plurality of patches, and
wherein the second patch sequence is different from the first patch sequence; and
a memory, shared by the first controller network and the second controller network,
wherein the first controller network is further configured to write data relating to a state of the first controller network to the memory,
wherein the second controller network is configured to read at least part of the data written by the first controller network from the memory and to utilize the data read, upon generating data indicative of at least one of the second patch segmentation mask candidates, and
wherein the computing device is further configured to generate, based on the data indicative of the first and second patch segmentation mask candidates, a final image segmentation mask for segmenting the N-dimensional medical image.

2. The system of claim 1, wherein the second controller network is further configured to write data relating to a state of the second controller network to the memory, and wherein the first controller network is configured to read at least part of the data written by the second controller network from the memory and to utilize the data read, upon generating data indicative of at least one of the first patch segmentation mask candidates.

3. The system of claim 2, wherein the second patch sequence equals the first patch sequence, reversed.

4. The system of claim 2, wherein the computing device is configured to implement at least one of at least one trained third neural network as a first memory write head usable by the first controller network for writing to the memory and at least one trained fourth neural network as a second memory write head usable by the second controller network for writing to the memory.

5. The system of claim 1, wherein the second patch sequence equals the first patch sequence, reversed.

6. The system of claim 1, wherein the computing device is configured to implement at least one of at least one trained third neural network as a first memory write head usable by the first controller network for writing to the memory and at least one trained fourth neural network as a second memory write head usable by the second controller network for writing to the memory.

7. The system of claim 6, wherein the computing device is configured to implement at least one of at least one trained fifth neural network as at least one first memory read head, usable by the first controller network for reading from the memory and at least one trained sixth neural network as at least one second memory read head, usable by the second controller network for reading from the memory, and wherein at least one of the at least one first memory read head and the at least one second memory read head is implemented as a differentiable transformation of context vectors representing the context data within the memory.

8. The system of claim 7, wherein the at least one first memory read head and the at least one second memory read head include at least one of a plurality of first memory read heads, and a plurality of second memory read heads.

9. The system of claim 1, wherein the computing device is configured to implement at least one of at least one trained fifth neural network as at least one first memory read head, usable by the first controller network for reading from the memory and at least one trained sixth neural network as at least one second memory read head, usable by the second controller network for reading from the memory, and wherein at least one of the at least one first memory read head and the at least one second memory read head is implemented as a differentiable transformation of context vectors representing context data within the memory.

10. The system of claim 9, wherein the at least one first memory read head and the at least one second memory read head include at least one of a plurality of first memory read heads, and a plurality of second memory read heads.

11. The system of claim 1, further comprising:

a database, shared by the first controller network and the second controller network, the database comprising key vectors linked to a plurality of datasets, wherein the computing device is configured to implement at least one of at least one trained seventh neural network as at least one first database read head usable by the first controller network and at least one trained eighth neural network as at least one second database read head usable by the second controller network, wherein at least one of the at least one first database read head, and the at least one second database read head is configured and usable to retrieve, based on the key vectors, data based on at least one of the plurality of datasets from the database; and wherein a respective one of at least one of the first controller network and second controller network is configured to utilize the data retrieved from the database upon generating data indicative of at least one of the first patch segmentation mask candidate and the second patch segmentation mask candidates, respectively.

12. The system of claim 1, wherein the computing device is configured to implement a trained ninth neural network as an encoder module, and wherein the encoder module is configured to receive patches from the input module and to generate the input data representing each of the plurality of patches for the first controller network and the second controller network.

13. The system of claim 1, wherein the computing device is further configured to generate, using the data indicative of the first patch segmentation mask candidates, data indicative of a first image segmentation mask candidate, to generate, using the data indicative of the second patch segmentation mask candidates, data indicative of a second image segmentation mask candidate, and to generate data indicative of a final image segmentation mask based on the first image segmentation mask and the second image segmentation mask candidate; and wherein the system further comprises a decoder module configured to generate, from the data indicative of the final image segmentation mask, the final image segmentation mask for segmenting the N-dimensional medical image.

14. The system of claim 13, wherein the computing device is further configured to implement a trained tenth neural network as the decoder module.

15. The system of claim 14, wherein the computing device is further configured to implement a trained eleventh neural network as a fusion module, and wherein the fusion module is configured to generate the data indicative of the final image segmentation mask based on the data indicative of the first image segmentation mask candidate and the second image segmentation mask candidate.

16. The system of claim 13, wherein the computing device is further configured to implement a trained eleventh neural network as a fusion module, and wherein the fusion module is configured to generate the data indicative of the final image segmentation mask based on the data indicative of the first image segmentation mask candidate and the second image segmentation mask candidate.

17. The system of claim 1, wherein all of the neural networks of the system are configured to be differentiable.

18. A method for medical image segmentation, comprising:

providing a plurality of patches of an N-dimensional medical image to be segmented;

sequentially receiving, by a first trained neural network acting as a first controller network, in a first patch sequence, input data representing each of the plurality of patches;

sequentially receiving, by a second trained neural network acting as a second controller network, input data representing each of the plurality of patches in a second patch sequence, sequentially generating and outputting, by the first controller network, data indicative of a respective first patch segmentation mask candidate for each of the plurality of patches;

sequentially generating and outputting, by the second controller network, data indicative of a respective second patch segmentation mask candidate for each of the plurality of patches, the second patch sequence being different from the first patch sequence;

writing, by the first controller network, data relating to a state of the first controller network, to a memory for at least the second controller network;

reading from the memory, by the second controller network, at least part of the data written by the first controller network;

utilizing, by the second controller network, the data read, upon generating data indicative of at least one of the second patch segmentation mask candidates; and generating, based on the data indicative of the first patch segmentation mask candidates and the second patch segmentation mask candidates, a final image segmentation mask for segmenting the N-dimensional medical image.

19. The method of claim 18, further comprising:

writing to a memory, by the second controller network, data relating to a state of the second controller network;

reading from the memory, by the first controller network, at least part of the data written by the second controller network; and utilizing, by the first controller network, the data read, upon generating data indicative of at least one of the first patch segmentation mask candidates.

20. A non-transitory computer-readably data storage medium storing executable program code, configured to, upon the program code being executed on a computer, perform the method of claim 18.

21. A non-transitory computer-readably data storage medium storing executable program code, configured to, upon the program code being executed on a computer, perform the method of claim 19.

* * * * *